United States Patent [19]

Chevallet et al.

[11] Patent Number: 5,441,636
[45] Date of Patent: Aug. 15, 1995

[54] INTEGRATED BLOOD TREATMENT FLUID MODULE

[75] Inventors: Jacques Chevallet, Serezin Du Rhone, France; Paul Priest; Keith Manica, both of Lakewood, Colo.

[73] Assignee: Cobe Laboratories, Inc., Lakewood, Colo.

[21] Appl. No.: 16,842

[22] Filed: Feb. 12, 1993

[51] Int. Cl.⁶ .................... B01D 35/00; B01D 36/00; B01D 61/28; B01D 61/30

[52] U.S. Cl. .................... 210/232; 210/239; 210/240; 210/321.6

[58] Field of Search .............. 210/195.2, 232, 239, 210/240, 249, 258, 321.6, 321.84, 416.1; 604/4, 5, 6; 137/861; 138/37, 111; 417/2, 12, 426, 427

[56] References Cited

U.S. PATENT DOCUMENTS

| | | |
|---|---|---|
| 2,835,252 | 5/1958 | Mauchel . |
| 3,489,145 | 1/1970 | Judson et al. . |
| 3,655,123 | 4/1972 | Judson et al. ............ 422/44 |
| 3,709,222 | 1/1973 | Devries ................ 417/395 |
| 3,737,251 | 6/1973 | Berman et al. .......... 417/12 |
| 3,774,762 | 11/1973 | Lichtenstein ........... 210/94 |
| 3,908,657 | 9/1975 | Kowarski ............. 128/767 |
| 3,912,455 | 10/1975 | Lichtenstein .......... 422/61 |
| 3,946,731 | 3/1976 | Lichtenstein .......... 210/87 |
| 3,963,023 | 6/1976 | Hankinson ............ 604/19 |
| 3,967,627 | 7/1976 | Brown ................ 607/104 |
| 4,069,968 | 1/1978 | Herman ................ 494/1 |
| 4,083,777 | 4/1978 | Hutchisson ........... 210/195.2 |
| 4,086,924 | 5/1978 | Latham, Jr. ............ 604/6 |
| 4,146,172 | 3/1979 | Cullis et al. ........... 494/17 |
| 4,185,629 | 1/1980 | Cullis et al. ........... 604/6 |
| 4,187,979 | 2/1980 | Cullis et al. ........... 494/1 |
| 4,197,847 | 4/1980 | Djerassi .............. 604/6 |
| 4,211,597 | 7/1980 | Lipps et al. .......... 156/245 |
| 4,223,672 | 9/1980 | Terman et al. ......... 210/927 |
| 4,253,456 | 3/1981 | Schindler et al. ....... 128/DIG. 13 |
| 4,263,808 | 4/1981 | Bellotti et al. ......... 73/714 |
| 4,300,551 | 11/1981 | Kinney ............... 128/637 |
| 4,379,452 | 4/1983 | Devries .............. 604/6 |
| 4,436,620 | 3/1984 | Bellotti et al. ........ 210/90 |
| 4,479,761 | 10/1984 | Bilstad et al. ......... 417/395 |
| 4,481,827 | 11/1984 | Bilstad et al. ......... 604/6 |
| 4,498,983 | 2/1985 | Bilstad et al. ......... 210/97 |
| 4,526,515 | 7/1985 | Devries .............. 417/63 |
| 4,637,813 | 1/1987 | Devries .............. 604/6 |
| 4,661,246 | 4/1987 | Ash ................. 210/195.2 |
| 4,861,242 | 8/1989 | Finsterwald .......... 417/477 |
| 5,174,894 | 12/1992 | Ohsawa et al. ........ 210/321.84 |
| 5,211,849 | 5/1993 | Kitaevich et al. ...... 210/645 |
| 5,234,608 | 8/1993 | Duff ................. 210/195.2 |

FOREIGN PATENT DOCUMENTS

| | | |
|---|---|---|
| 0134436 | 3/1985 | European Pat. Off. . |
| 0240154 | 10/1987 | European Pat. Off. . |
| 0373455 | 12/1989 | European Pat. Off. . |
| 2390173 | 12/1978 | France . |
| 2619603 | 2/1989 | France . |

Primary Examiner—John Kim
Attorney, Agent, or Firm—Sheridan Ross & McIntosh

[57] ABSTRACT

An integrated blood treatment fluid module is provided having particular multi-function application in the treatment of renal failure. The module comprises a support member, a blood treatment device mounted to the support member, and multiple fluid circuits, wherein a plurality of the fluid circuits are interconnected to the support member and at least one of the fluid circuits is fluidly connected to the blood treatment device. At least two of the fluid circuits are interconnected with the support member so as to have a portion of each disposed in a U-shape, each U-shape portion extending in a different direction, for selective positioning about a corresponding peristaltic pump of a blood treatment apparatus. For renal treatment applications, the blood conditioning device may be a hemofiltration device, hemodialysis device or high-flux dialyzer. In such applications, a blood supply circuit is fluidly connected to a blood input port of the blood treatment device, a blood return circuit is fluidly connected to a blood output port of the blood treatment device, and a waste fluid circuit is fluidly connected to a waste output port of the blood treatment device. A treatment fluid circuit is also fluidly connected to a treatment fluid input port of the blood treatment device. A replacement fluid circuit can be fluidly connected with one of either the blood supply circuit or blood return circuit, and an anticoagulant fluid circuit can be fluidly interconnected to the blood supply circuit.

13 Claims, 6 Drawing Sheets

INTEGRATED BLOOD TREATMENT FLUID MODULE

FIELD OF THE INVENTION

This invention pertains to blood treatment systems, and more specifically to an integrated blood treatment fluid module which is particularly apt for multi-function treatment of renal failure.

BACKGROUND OF THE INVENTION

The utilization and modalities of blood treatment systems is ever increasing. Such systems typically entail the in-line withdrawal of blood from a patient, extracorporeal treatment of the blood by a blood treatment apparatus, and return of the blood to the patient. In order to achieve such blood transfer, as well as remove and/or introduce components into the blood stream, as may be desired, multiple fluid circuits and pumps may be employed.

Blood treatment systems have been developed to carry out various treatments such as therapeutic and non-therapeutic plasmapheresis, extracorporeal blood oxygenation, and blood purification and water removal in the case of renal failure. The present invention will be described in connection with renal failure. However, it is to be understood that this particular example is given purely by way of illustration and is not intended to limit the scope of the invention as claimed. For palliating renal failure blood treatment devices are used to perform renal functions, such as dialyzers for hemodialysis wherein undesired waste components are removed from the blood (e.g., urea and creatinine) and desired electrolyte balance in the blood is established (e.g., sodium ions). This is typically achieved by counterflowing blood and an isotonic liquid, i.e., dialysate, on opposite sides of the dialyzer membrane which allows for diffusive transfer therethrough. Blood treatment devices, namely hemofilters or high-flux dialysers, are also employed for hemofiltration wherein undesired water and certain impurities are removed from blood. This is typically accomplished by flowing blood past a high-permeability membrane across which a negative pressure gradient is established to achieve convective transfer. A fluid substitute is introduced into the blood as necessary. High-flux dialyzers allow also for achieving hemodiafiltration, which consists of simultaneous hemodialysis and hemofiltration.

In order to implement such renal failure treatment techniques, multiple fluid circuits, pump means and blood conditioning devices may be incorporated in a blood therapy apparatus. Further, it should be appreciated that since all such components contact body fluids during use, they must be disposed of and replaced between uses. To date this has entailed the separate handling of multiple components, which, before each treatment session, must be assembled together and mounted on the blood treatment apparatus. This handling is time-consuming, entails the risk of an erroneous assembling and mounting of the multiple components and the risk of breaching their sterility, and also requires experienced operators, such handling being out of reach of the patients themselves.

SUMMARY OF THE INVENTION

The present invention is an integrated blood treatment fluid module which can be readily mounted on a blood treatment apparatus and which has particular multi-function utility in the treatment of renal failure. The invention reduces pre and post procedure handling and interconnection requirements, is space efficient, and lends itself to prepackaging and disposability. Further, the components and assembly of the inventive module allow for cost-effective production. Numerous additional advantages will be apparent to those skilled in the art.

As used herein, the term "blood treatment device" means any device for removing components from and/or introducing components into a blood stream, including plasmapheresis, oxygenation, hemodialysis, hemofiltration and hemodiafiltration treatment devices.

The invention comprises a support member, a blood treatment device mounted on the support member, and a plurality of fluid circuits interconnected with the support member. At least one of the fluid circuits is fluidly connected to the blood treatment device, and at least two of the fluid circuits are disposed relative to the support member to define a U-shaped portion in each such fluid circuit for ready interface with one or more corresponding peristaltic pumps of a blood treatment apparatus. Each U-shaped portion is oriented in a different direction. The support member preferably has a plurality of side edges defining a polygon shape, wherein each U-shaped fluid circuit portion extends laterally from a different one of the side edges for ease of handling and contemporaneous placement of the U-shaped portions relative to corresponding peristaltic pumps of the blood treatment apparatus. In this regard, the side edges of the polygonal support structure and U-shaped fluid circuit portions may be in one-to-one relation for space efficiency and for ready positioning of the U-shaped portions relative to a corresponding number of peristaltic pumps on a blood treatment apparatus, the pumps being arranged so that one pump mates with each U-shaped portion.

In one embodiment of the present invention, an integrated, multi-function blood treatment fluid module is provided for renal failure treatment applications. Specifically, a high-flux dialyzer is mounted along the longitudinal axis of a diamond-shaped support plate which is sized to fit between four peristaltic pumps disposed in a rectangular manner on a blood treatment apparatus. Multiple fluid circuits are also mounted on and oriented relative to the diamond-shaped plate via multiple connection members. A different fluid circuit is disposed in a U-shaped manner relative to each of the side edges of the plate for contemporaneous engagement with corresponding peristaltic pumps of a blood treatment apparatus.

A blood supply fluid circuit is included having a connector at one end for selective interconnection with a blood access device such as a catheter assembly and being fluidly connected at its other end to a blood input port of the high-flux dialyzer. A blood return fluid circuit is interconnected at one end to a blood outlet port of the high-flux dialyzer and has a connector at the other end for selective interconnection with a blood access device such as a catheter assembly. A replacement fluid circuit, having a connector at one end for selective interconnection with a replacement fluid reservoir or a bicarbonate solution reservoir is fluidly connected at its other end with the blood supply fluid circuit for pre-conditioning dilution. Alternatively, the replacement fluid circuit can be fluidly connected with the blood return fluid circuit for post-conditioning dilution, as may be preferable or otherwise desired for a given treatment regime. An anticoagulant fluid circuit may also be utilized having a connector at one end for selective interconnection with an anticoagulant reservoir and pump assembly, and being fluidly connected at its other end to the blood supply fluid circuit upstream of the high-flux dialyzer. The anticoagulant reservoir and pump assembly can be a syringe pump. A treatment fluid (dialysate) circuit is also included having a connector at one end for selective connection with a treatment fluid reservoir assembly and being fluidly connected at its other end to a treatment fluid inlet port of said high-flux dialyzer. A waste fluid circuit is interconnected at one end to a waste outlet of the high-flux dialyzer and has a connector at its other end for selective interconnection with a waste reservoir assembly. Portions of the blood supply, replacement, treatment and waste fluid circuits are each separately disposed in a U-shape relative to different side edges of the diamond-shaped plate (i.e., one U-shaped portion per edge) for contemporaneous placement on corresponding peristaltic pumps of the blood treatment apparatus.

As will be appreciated, the described embodiment can be utilized for both chronic and acute renal failure treatment, and accommodates both venous and arterial blood supply and return arrangements. Further, the embodiment can be utilized for hemodialysis, for hemofiltration and for hemodiafiltration. Further, the blood treatment fluid module according to the invention is suitable for conventional dialysis, where the dialysate contains the principal electrolytes of blood, including bicarbonate, as well as for so called "buffer free" dialysis, where the dialysate does not contain any bicarbonate, and a bicarbonate solution is perfused to the patient during the dialysis session.

DETAILED DESCRIPTION

Figure 1:
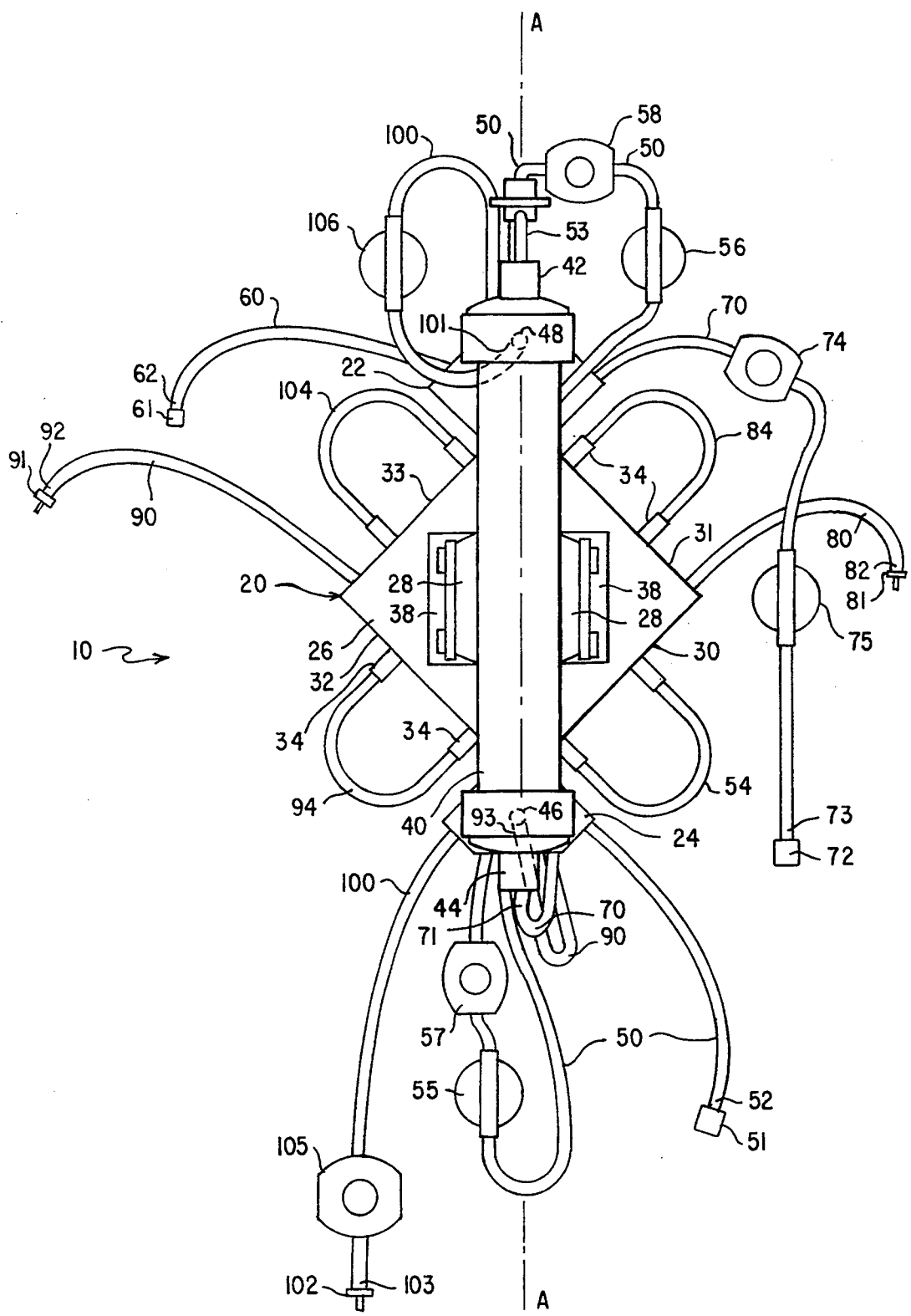
FIG. 1 is a front view of one embodiment of an integrated blood treatment fluid module embodying the present invention, as adapted for multi-function renal failure treatment applications.

FIGS. 1–4 are directed to an embodiment of the present invention and a schematic fluid flow representation of such embodiment as employed with a blood treatment apparatus as may be employed for multi-function treatment of renal failure.

Specifically, blood treatment fluid module 10 comprises a support plate 20 with a hollow fiber, high-flux dialyzer 40 and multiple interconnected fluid circuits 50, 60, 70, 80, 90, and 100 mounted thereupon. Support plate 20 is diamond-shaped with upper and lower diamond-shaped projections 22, 24, extending along a common longitudinal axis AA. High-flux dialyzer 40 is vertically interconnected to a front surface 26 of support plate 20 along such longitudinal axis AA by support legs 28, and includes blood inlet port 42, blood output port 44, treatment fluid input port 46, and waste outlet port 48. A plurality of connection members 34, 36 are provided on support plate 20 for holding fluid circuits 50, 60, 70, 80, 90 and 100. Specifically, a pair of gutter members 34 extend from each of the four side edges 30, 31, 32 and 33 of plate 20 and numerous seat members 36, such as clips, extend away from the back surface 27 of plate 20. Alternatively, in place of the seat members 36, plate 20 could be provided with a series of grooves defining paths for the various circuits, advantageously preventing them from kinking (e.g., during sterilization).

Figure 2:
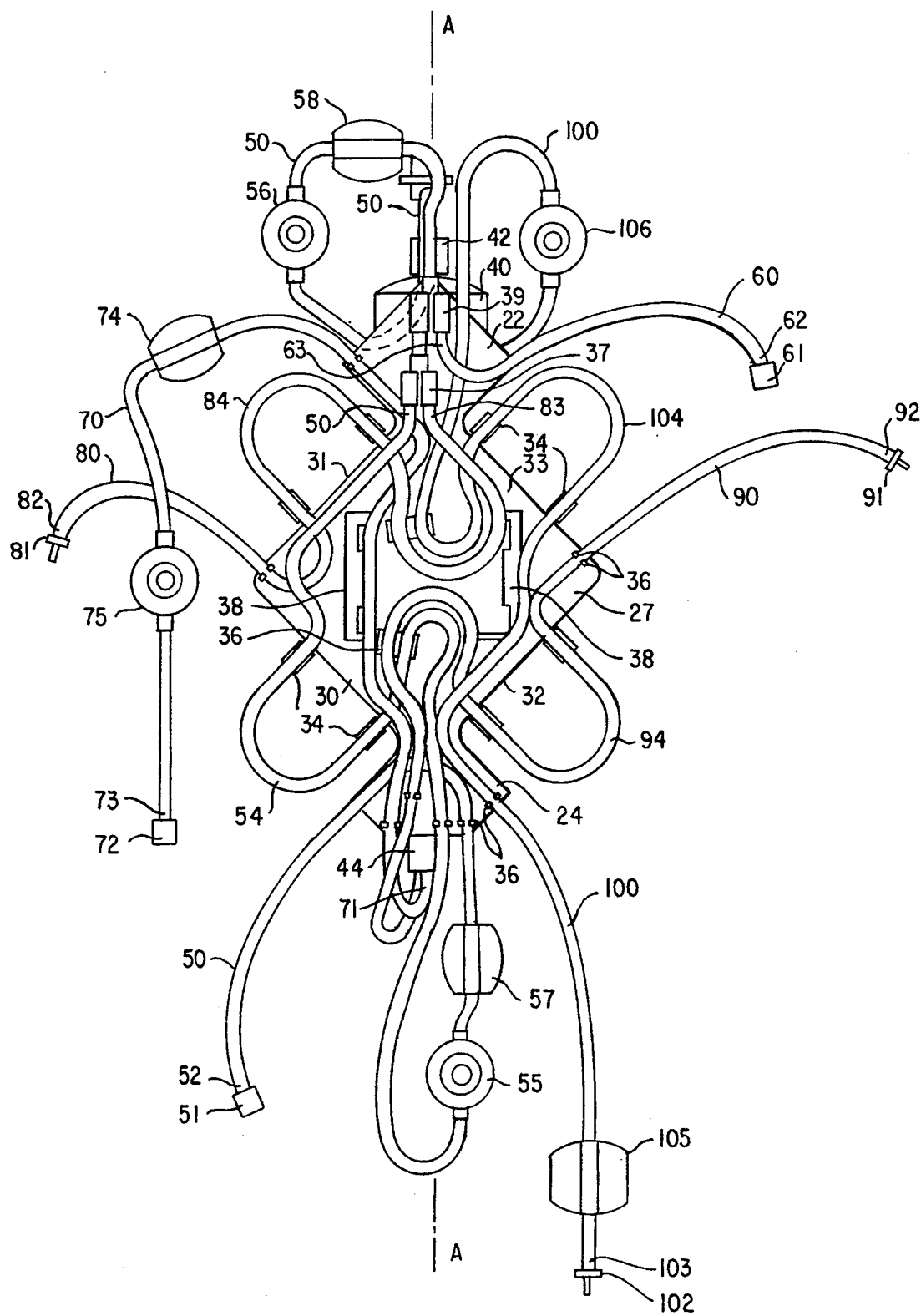
FIG. 2 is a rear view of the embodiment shown in FIG. 1.

Blood supply circuit 50 has a Luer connector 51 at one end 52 for selective interconnection with a catheter assembly and is fluidly connected at its other end 53 to blood input port 42 of high-flux dialyzer 40. The blood supply circuit 50 is held by a pair of the gutter members 34 relative to side edge 30 of support plate 20 to define a U-shaped portion 54 extending laterally outward from side edge 30. In-line pressure monitoring chambers 55 and 56 may be disposed upstream and downstream, respectively, of U-shaped portion 54. In-line blood sampling ports 57 and 58 may be included immediately upstream of pressure monitoring chambers 55 and 56, respectively. As illustrated in FIG. 2, blood supply circuit 50 sequentially passes through first and second Y-shaped circuit merge members 37 and 39 extending from the back of support plate 20 and located upstream of the high-flux dialyzer 40.

Anticoagulant fluid circuit 60 has a Luer connector 61 at one end 62 for selective engagement with an anticoagulant pump and reservoir assembly (e.g., a syringe pump comprising heparin solution) and is interconnected at its other end 63 to the second circuit merge member 39.

Blood return circuit 70 is fluidly connected at one end 71 to blood outlet port 44 of hemodiafiltration device 40 and has a Luer connector 72 at its other end 73 for selective interconnection with a catheter assembly. Blood return circuit 70 may include an in-line blood sampling port 74 and an in-line pressure monitoring chamber 75.

Replacement fluid circuit 80 has a spike connector 81 at one end 82 for selective interconnection with a replacement solution or bicarbonate solution reservoir assembly and is fluidly connected at its other end 83 to the first circuit merge member 37 for pre-conditioning dilution of the blood stream, or introduction of a bicarbonate solution as may be desired. Therebetween, fluid replacement circuit 80 is held by a pair of gutter members 34 relative to side edge 31 to define a U-shaped portion 84. As will be appreciated, first circuit merge member 37 could alternatively be positioned in the blood return circuit 70 downstream of high-flux dialyzer 40, and fluidly interconnected with replacement fluid circuit 80, for post-conditioning dilution of the bloodstream, as may be preferred.

Treatment fluid circuit 90 has a spike connector 91 at one end 92 for selective interconnection with a blood treatment fluid reservoir assembly (e.g., comprising dialysate) and is fluidly connected at its other end 93 to the treatment fluid inlet port 46 of high-flux dialyzer 40. Therebetween, treatment fluid circuit 90 is held by a pair of gutter members 34 relative to side edge 32 to define a U-shaped portion 94.

Waste fluid circuit 100 is fluidly connected at one end 101 to the waste outlet port 48 of high-flux dialyzer 40 and has a spike connector 102 at its other end 103 for selective interconnection with a fluid waste reservoir assembly. Such an assembly may, alternatively, be preconnected to spike connector 102. Between ends 101 and 103, waste fluid circuit 100 is held by a pair of gutter members 34 relative to side edge 33 to define a U-shaped portion 104. An in-line pressure monitoring chamber 105 may be provided between end 101 and U-shaped portion 104, and an in-line blood sampling port 106 may be provided between U-shaped portion 104 and end 103.

By way of example, support plate 20, legs 28 and connection members 34, 36 may be of molded plastic construction. Fluid circuits 50, 60, 70, 80, 90 and 100 are preferably of flexible transparent tubing construction, all of such tubing preferably having common cross-sectional dimensions. The unconnected ends of the various circuits (as packaged) may be provided with conventional plugs, thereby accommodating selective modes of operation, as will be further described. The entire blood conditioning/fluid circuit module is preferably sealed within sterile packaging for distribution, and may be readily disposed of after use.

Figure 3:
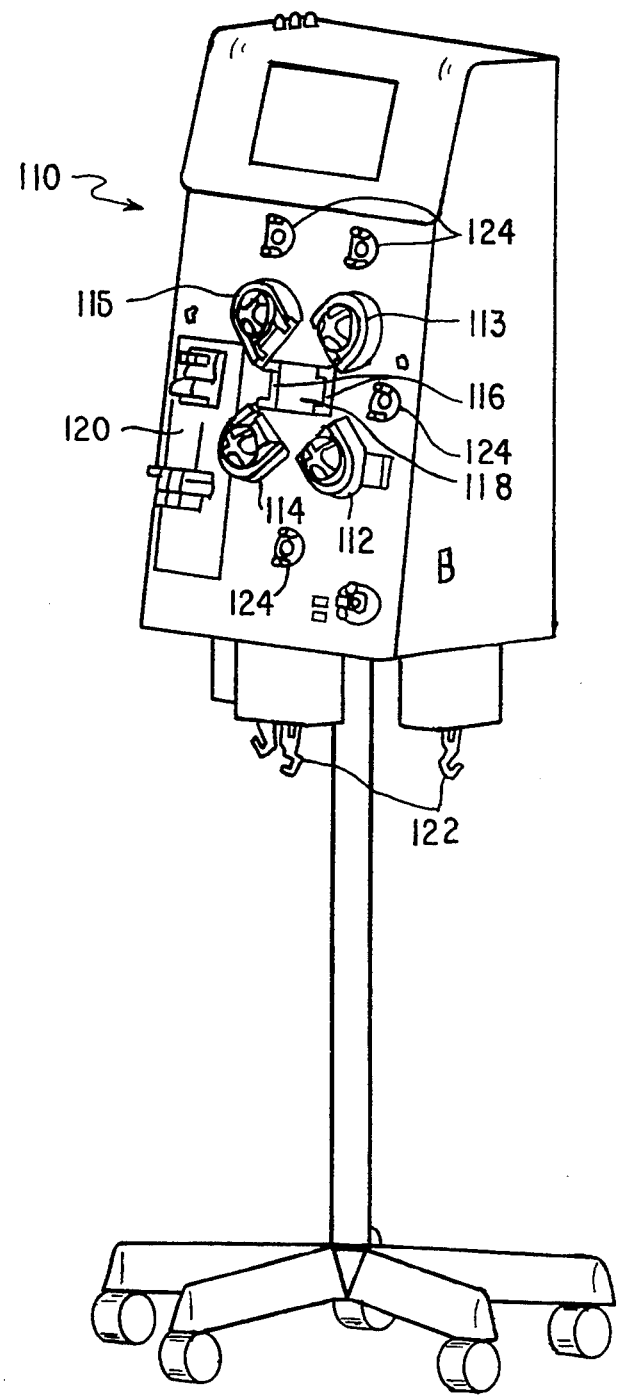
FIG. 3 is a perspective view of a blood treatment apparatus on which the embodiment shown in FIG. 1 may be employed.
Figure 4:
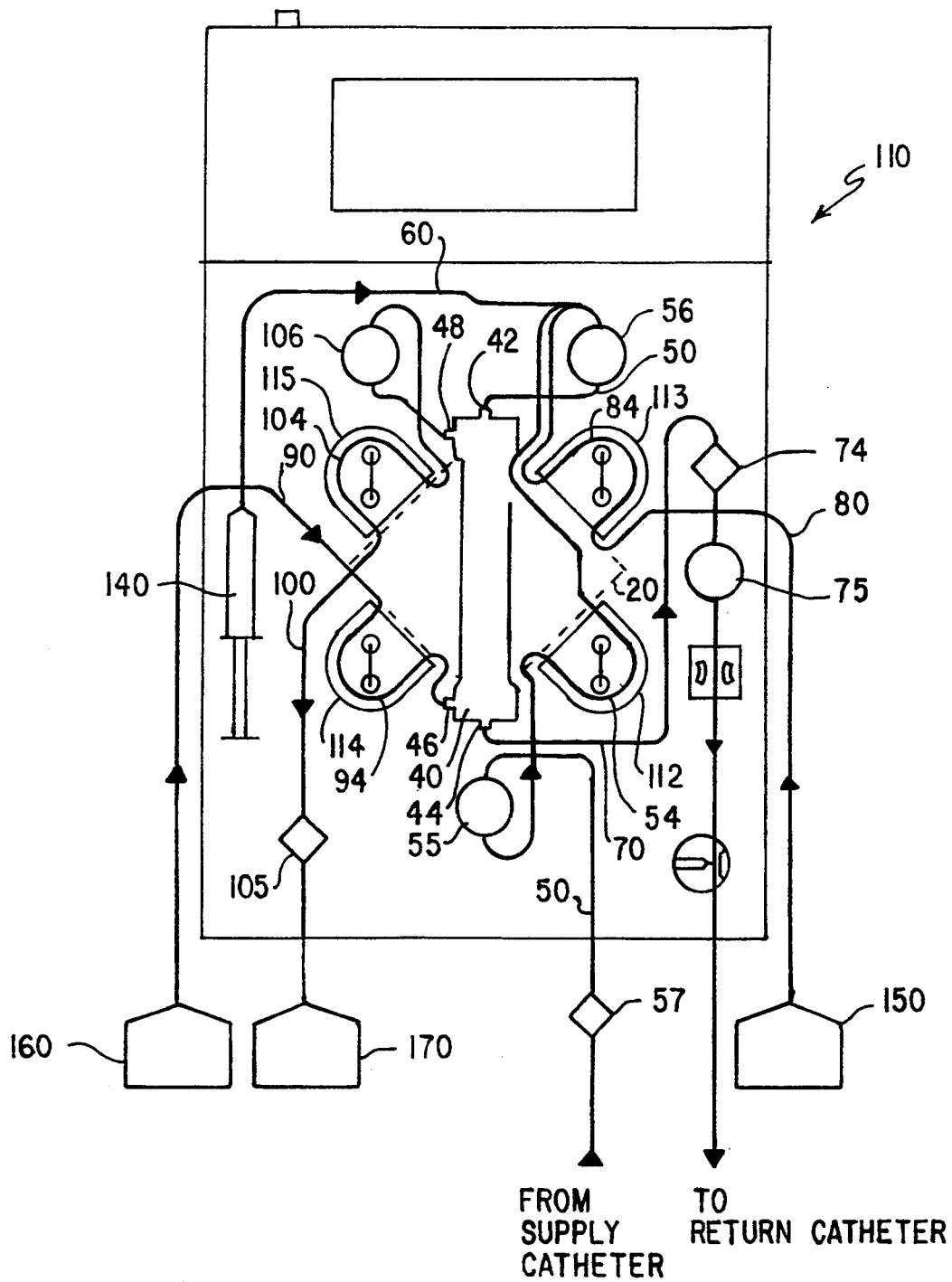
FIG. 4 is a schematic fluid flow representation of the embodiment shown in FIGS. 1 and 2 as operatively interconnected with the blood treatment apparatus of FIG. 3.

The illustrated blood treatment fluid circuit module 10 can be readily mounted on a blood treatment apparatus such as blood treatment apparatus 110 shown in FIGS. 3 and 4. More particularly, support plate 20 may be sized for positioning between four rectangularly disposed peristaltic pumps 112, 113, 114 and 115 of blood treatment apparatus 110, wherein each of the U-shaped portions 54, 84, 94, and 104, of blood supply fluid circuit 50, replacement fluid circuit 80, treatment fluid circuit 90 and waste fluid circuit 100, respectively, can be contemporaneously positioned about corresponding peristaltic pumps 112, 113, 114,115, respectively. By way of example, interconnection between blood treatment fluid module 10 and the blood treatment apparatus 110 may be established by selective engagement between engaging fingers 116 extending from a carrier 118 of blood treatment apparatus 110 into receiving apertures 38 of support plate 20. Such carrier 118, and thus engaging fingers 116, may be disposed for retraction into blood treatment apparatus 110 so as to establish operative interface between said U-shaped portions 54, 84, 94 and 104 and peristaltic pumps 112, 113, 114 and 115, respectively, as desired. Such operative interface only allows for fluid flow through fluid circuits 50, 80, 90 or 100, when the corresponding peristaltic pump 112, 113, 114 or 115, respectively, is operated; each of such fluid circuits being otherwise occluded by its corresponding pump.

Certain types of treatment, in particular the treatments used for palliating acute renal failure, may require a continuous operation of the pumps 112, 113, 114, or 115 for long periods of time (typically several days), with low flow rates of the liquids circulated by these pumps. Conventional peristaltic pumps with removable rotors (comprising, for example, a rotor secured by means of a bayonet mount at the end of the shaft of a DC motor) are not particularly adapted to this operation mode, for the life span of a DC motor operated continuously is limited. Further, given that DC motors have a limited speed range, the only way to achieve the widely different flow rates entailed is to adjust the diameter of the tubing used for a given fluid circuit. And as the flow rates for the various fluid circuits of the integrated fluid circuit module disclosed herein may be substantially different, by using DC motors for rotating the various pumps it is necessary to mount on such module tubings having flow rates required for the various diameters corresponding to the various circuits and that complicates the manufacturing process.

Consequently, the use of stepper motors in place of conventional DC motors can solve the above problems, since the life span of such motors, for the same use, is generally much longer than the life span of DC motors, and their ability to rotate at a wide range of speeds allows for fitting the module with tubing lengths having the same diameter for all of the various circuits.

However, stepper motors connected to conventional removable rotors generate, in operation, significant audible noise.

Figure 8:
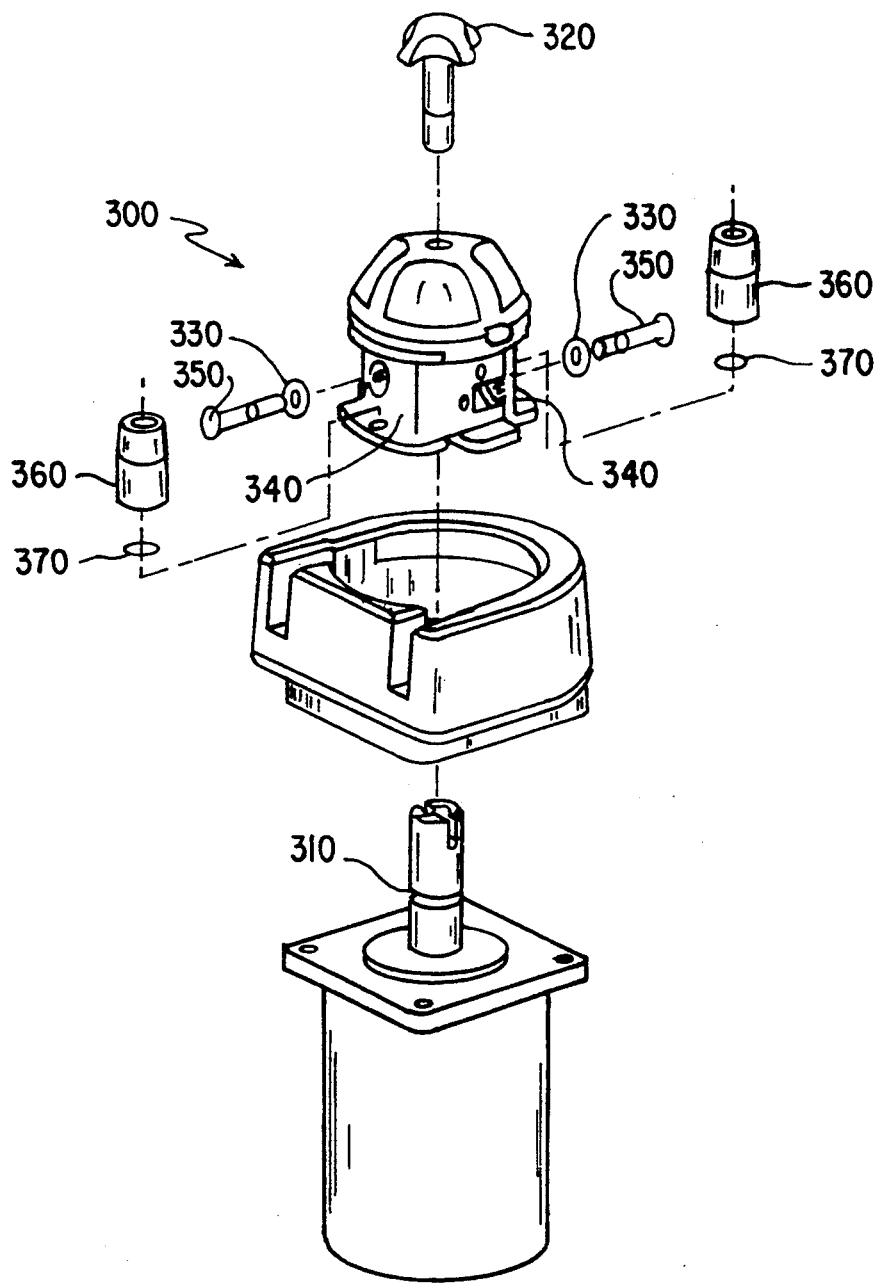
FIG. 8 is an exploded perspective view of an improved peristaltic pump that can be employed in the blood treatment apparatus of FIG. 3.

A modified rotor allows for substantially silent operation of a peristaltic pump driven by a stepper motor. In particular, relative to conventional rotors, three modifications can be made, as reflected in FIG. 8: The rotor 300 is secured to the stepper motor shaft 310 by means of a hand screw 320 and no longer by means of a bayonet mount; an elastomer damper 330 is interposed between each spring loaded pivot arm 340 and the head of the screw 350 limiting the outward rotation of the pivot arm 340; and each roller 360 is mounted on the corresponding pivot arm 340 by means of a wave spring washer 370 which resiliently urges the roller upwards.

To prepare for use, blood treatment fluid module 10 can be quickly and easily interconnected with the blood treatment apparatus 110 illustrated in FIGS. 3 and 4. First, support plate 20 is engaged on carrier 118 as described above, and carrier 118 is then retracted to establish operative interface between U-shaped portions 54, 84, 94, and 104, and corresponding peristaltic pumps 112, 113, 114, and 115. Next, the various in-line pressure monitoring chambers provided with blood treatment fluid module 10 are connected to corresponding pressure sensors 124. The anticoagulant fluid circuit 60 is then connected to syringe 140 which is mounted on holder 120. Waste fluid circuit 100 is connected to the waste fluid reservoir assembly 170, which in turn is hooked at the corresponding scale 122. The foregoing steps are typically executed regardless of the type of treatment to be carried out.

If the treatment chosen is slow ultrafiltration, the only remaining preparation would be to connect blood supply and return circuits 50,70 to the patient after initial rinsing and filling (i.e., priming) of the circuits to be used during the treatment session. Treatment fluid circuit 90 and replacement fluid circuit 80 are not used for such treatment and the plugs at the respective free ends thereof are therefore left in place.

If the treatment chosen is hemofiltration, the replacement fluid circuit 80 is connected to the replacement fluid reservoir assembly 150, which is hooked to the corresponding scale 122. The treatment fluid circuit 90 is not used and the plug at the free end thereof is therefore left in place.

If the treatment chosen is conventional hemodialysis, the treatment fluid circuit 90 is connected to the treatment fluid reservoir assembly 160, which is hooked at the corresponding scale 122. The replacement fluid circuit 80 is not used and the plug at the free end thereof is therefore left in place.

If the treatment chosen is "buffer-free" hemodialysis, the treatment circuit 90 is connected to the treatment fluid reservoir assembly 160, which contains a dialysate without bicarbonate and is hooked to the corresponding scale 122. The replacement fluid circuit 80 is connected to the replacement fluid reservoir assembly 150 which contains a bicarbonate solution and is hooked to the corresponding scale 122.

Finally, if the treatment chosen is hemodiafiltration, the treatment fluid circuit 90 and the replacement fluid circuit 80 are respectively connected to the treatment fluid reservoir assembly 160 and to the replacement fluid reservoir assembly 150 which are each hooked to corresponding scales 122.

Whatever treatment is selected, when the circuits to be used have been primed, the blood supply and return circuits 50,70 are connected to the patient and the treatment session can be initiated by operation of the appropriate pumps, and in particular, the blood pump 112 when the supply fluid circuit 50 is interconnected to the vein of the patient.

Numerous modifications to and applications of the present invention are possible. For example, while the above-described embodiment contemplates use in a venous blood supply arrangement, the invention can also be readily employed in arterial blood supply situations. In such situations, for example, U-shape portion 54 of blood supply circuit 50 would not need to be positioned for operative interface with a peristaltic pump since the arterial blood pressure of the patient could be used to transfer the blood through blood supply circuit 50 and blood return circuit 70. Further, and by way of example only, it can be readily appreciated that support plate 20 could be pentagonal, and a U-shaped portion of anticoagulant fluid circuit 60 could be defined relative to a side edge of the support plate 20 for operative interface with an additional peristaltic pump of a blood treatment apparatus.

Figure 5:
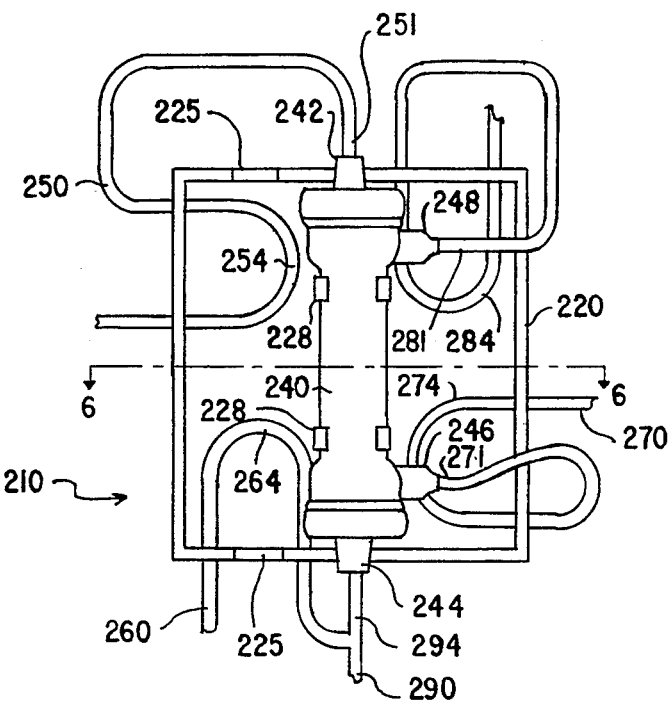
FIG. 5 is a front view of an alternate embodiment of an integrated blood treatment fluid module comprising the present invention.
Figure 6:
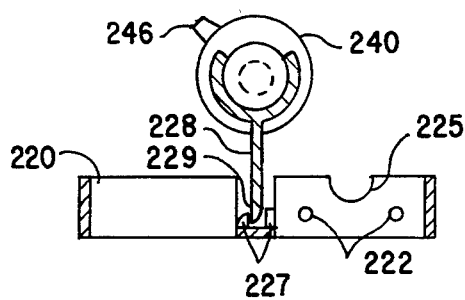
FIG. 6 is a cross section view of the embodiment shown in FIG. 5 (with fluid circuits removed for purposes of illustration), taken along line 6—6.
Figure 7:
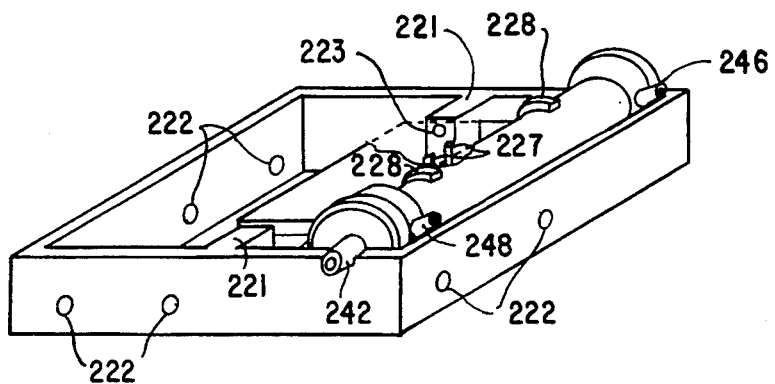
FIG. 7 is a rear perspective view of the embodiment shown in FIG. 5 (with fluid circuits removed for purposes of illustration).

FIGS. 5–7 show a further alternate blood treatment fluid module 210, comprising a rectangular support frame 220, with a high-flux dialyzer 240 and multiple fluid circuits 250, 260, 270 and 280 mounted thereupon. Blood supply circuit 250, replacement fluid circuit 260, blood treatment fluid circuit 270, and waste fluid circuit 280 each pass through holes 222 in frame 220 to define U-shaped portions 254, 264, 274 and 284, respectively, extending laterally inward relative to different side edges of frame 220. As such, compactness is enhanced and U-shaped portions 254, 264, 274, and 284 are advantageously protected within support frame 220.

Relatedly, high-flux dialyzer 240 is interconnected to support frame 220 by a support leg 228, which is hinged to centrally disposed struts 221 by lateral extensions (not shown) that fit into apertures 223 on struts 221. Consequently, high-flux dialyzer 240 can be at least partially nested within support frame 220 and seats 225 thereof for packaging as shown by the rear perspective, partial cutaway view of FIG. 7 (with fluid circuits removed for purposes of illustration); and pivoted to an operative position where it is "locked" by virtue of angled or rounded end 229 of the support leg 228 being restrained between opposing edge portions 227 on struts 221, as shown by FIGS. 5 and 6. It should be appreciated that compact packaging of module 210 reduces not only packaging costs, but also costs associated with sterilization, storage and transport.

Blood supply circuit 250 is fluidly connected at one end 251 to a blood input port 242 of high-flux dialyzer 240. A blood return circuit 290 is fluidly connected at one end 291 to a blood output port 244 of high-flux dialyzer 240, and replacement fluid circuit 260 is fluidly interconnected at junction 300 with blood return circuit 290. Blood conditioning circuit 270 is fluidly connected at one end 271 to a treatment fluid input port 246 of high-flux dialyzer 240, and waste fluid circuit 280 is fluidly connected at one end 281 to a waste output port 248 of high-flux dialyzer 240. As will be appreciated, additional components and features could be included per the previously described embodiment.

In view of the foregoing, numerous additional modifications of the present invention will be apparent to those in the art, and are intended to be within the scope of the following claims.

What is claimed is:

1. An integrated blood treatment fluid module for continuous in-line, extra-corporeal blood treatment on a blood treatment apparatus comprising:
   a rectangular support member having side edges defining a rectangular shape and having means for selective interconnection of the module to and selective disconnection of the module from a blood treatment apparatus;
   a blood treatment device defined apart from and mounted on said support member, said blood treatment device being centered about an axis lying in a plane that diagonally bisects the rectangular support member; and,
   a plurality of fluid circuits supportably interconnected with and oriented in predetermined positions relative to said support member, at least two of the fluid circuits being supportably interconnected to and thereby disposed in an outwardly extending U-shape relative to said support member with each U-shape portion extending from a different one of said side edges and in a different direction, and at least two of the fluid circuits being fluidly connected to said blood treatment device.

2. An integrated blood treatment fluid module, as claimed in claim 1:
   wherein each of said U-shape portions extends laterally in an inverted manner from a different one of a plurality of side edges of the support member.

3. An integrated blood treatment fluid module, as claimed in claim 2:
   wherein said U-shaped portions are disposed in one-to-one relation with said side edges of the support member.

4. An integrated blood treatment fluid module, as claimed in claim 1, said blood treatment fluid module being for use in the treatment of renal failure:
   wherein said blood treatment device is selected from a group consisting of hemofiltration device, hemodialysis device and high-flux dialyzer; and
   wherein a first of said fluid circuits is fluidly connected to a blood supply port of said blood treatment device, a second of said fluid circuits is fluidly connected to a blood return port of said blood treatment device, and a third of said fluid circuits is fluidly connected to a waste outlet port of said blood treatment device.

5. An integrated blood treatment fluid module, as claimed in claim 4:
wherein at least said third of said fluid circuits is disposed relative to the support member to define a U-shaped portion in the third circuit.

6. An integrated blood treatment fluid module, as claimed in claim 4:
wherein one of either said first or second fluid circuits is fluidly connected to a different one of said plurality of fluid circuits.

7. An integrated blood treatment fluid module, as claimed in claim 6:
wherein said first and third fluid circuits are each disposed relative to the support member to define a U-shaped portion in each of the first and third circuits; and,
wherein said different one of said plurality of fluid circuits is disposed relative to the support member to define a U-shaped portion.

8. An integrated blood treatment fluid module, as claimed in claim 4:
wherein a fourth of said fluid circuits is fluidly connected to a blood treatment fluid inlet port of said blood treatment device.

9. An integrated blood treatment fluid module, as claimed in claim 8:
wherein one of either said first or second fluid circuits is fluidly connected to a different one of said plurality of fluid circuits, said different one of said fluid circuits being disposed relative to the support member to define a U-shaped portion in the different one of the fluid circuits; and,
wherein said first, third and fourth fluid circuits are each supportably interconnected to and thereby disposed relative to the support member to define a U-shaped portion in each of the first, third and fourth fluid circuit.

10. An integrated blood treatment fluid module, as claimed in claim 1, wherein the module is sealed within sterile packaging prior to use.

11. An integrated blood treatment fluid module, as claimed in claim 1, wherein said blood treatment device is mounted on said support member in a substantially non-overlapping position relative to all of said U-shape fluid circuit portions.

12. An integrated blood treatment fluid module comprising:
a support member having means for selective interconnection of the module to and selective disconnection of the module from a blood treatment apparatus;
a blood treatment device defined apart from and hingedly mounted on said support member for pivotal movement relative thereto, wherein said blood treatment device is positionable to be at least partially nested within said support member; and
a plurality of fluid circuits interconnected with said support member, at least two of the fluid circuits being disposed to have U-shaped portions relative to the said support member with each U-shape portion extending in a different direction, and at least two of the fluid circuits being fluidly connected to said blood treatment device.

13. An integrated blood treatment fluid module comprising:
a support member having horizontal and vertical axes, and having means for selective interconnection of the module to and selective disconnection of the module from a blood treatment apparatus;
a blood treatment device defined apart from and mounted on said support member, said blood treatment device being centered about one of said horizontal and vertical axes of said support member; and,
a plurality of fluid circuits supportably interconnected with and oriented in predetermined positions relative to said support member, at least two of the fluid circuits being supportably interconnected to and thereby disposed in an outwardly extending U-shape relative to said support member with each U-shape portion extending outwardly in a different direction between and relative to said horizontal and vertical axis, and at least two of the fluid circuits being fluidly connected to said blood treatment device.

* * * * *

UNITED STATES PATENT AND TRADEMARK OFFICE
CERTIFICATE OF CORRECTION

PATENT NO. : 5,441,636
DATED : August 15, 1995
INVENTOR(S) : PRIEST et al.

It is certified that error appears in the above-indentified patent and that said Letters Patent is hereby corrected as shown below:

Column 8,

In Claim 2, line 1, please delete "2." and insert therefor -- 4. -- and also on line 1, please delete "claim 1" and insert therefor -- claim 3 --;

In Claim 3, line 1, please delete "3." and insert therefor -- 5. --, and also on line 1, please delete "claim 2" and insert therefor -- claim 4 --;

In Claim 4, line 1, please delete "4." and insert therefor -- 6. --, and also on line 1, please delete "claim 1" and insert therefor -- claim 3 --;

Column 9,

In Claim 5, line 1, please delete "5." and insert therefor -- 7. --, and also on line 1, please delete "claim 4" and insert therefor -- claim 6 --;

In Claim 6, line 1, please delete "6.." and insert therefor -- 8. --, and also on line 1, please delete "claim 4" and insert therefor -- claim 6 --;

In Claim 7, line 1, please delete "7." and insert therefor -- 9. --; line 2, delete "claim 6" and insert --claim 8 --.

In Claim 8, line 1, please delete "8." and insert therefor -- 10. --, and also on line 1, please delete "claim 4" and insert therefor -- claim 6 --;

In Claim 9, line 1, please delete "8." and insert therefor -- 11. --, and also on line 1, please delete "claim 8" and insert therefor -- claim 10 --;

UNITED STATES PATENT AND TRADEMARK OFFICE
CERTIFICATE OF CORRECTION

PATENT NO. : 5,441,636
DATED : August 15, 1995
INVENTOR(S) : PRIEST et al.

It is certified that error appears in the above-indentified patent and that said Letters Patent is hereby corrected as shown below:

In Claim 10, line 1, please delete "10." and insert therefor -- 12. --, and also on line 1, please delete "claim 1" and insert therefor -- claim 3 --;

In Claim 11, line 1, please delete "11." and insert therefor -- 13. --, and also on line 1, please delete "claim 1" and insert therefor -- claim 3 --;

In Claim 12, line 1, please delete "12." and insert therefor -- 2. --;

In Claim 13, line 1, please delete "13." and insert therefor -- 3. --;

Signed and Sealed this

Twenty-first Day of November, 1995

Attest:

BRUCE LEHMAN

Attesting Officer    Commissioner of Patents and Trademarks